(12) United States Patent
Wong

(10) Patent No.: US 6,626,194 B2
(45) Date of Patent: Sep. 30, 2003

(54) ELECTRIC SHAVER CLEANING APPARATUS

(75) Inventor: Ying Man Wong, Hong Kong (HK)

(73) Assignee: Raymond Electric (China) Limited (HK)

( * ) Notice: Subject to any disclaimer, the term of this patent is extended or adjusted under 35 U.S.C. 154(b) by 111 days.

(21) Appl. No.: 09/858,936

(22) Filed: May 16, 2001

(65) Prior Publication Data

US 2002/0170583 A1 Nov. 21, 2002

(51) Int. Cl.$^7$ .............................. B08B 3/00; B08B 3/10
(52) U.S. Cl. ................... 134/102.2; 134/102.1; 134/111; 134/143; 134/155; 134/182; 134/186
(58) Field of Search .............. 134/102.1, 102.2, 134/111, 143, 155, 182, 186

(56) References Cited

U.S. PATENT DOCUMENTS

| | | | |
|---|---|---|---|
| 1,866,519 A | * 7/1932 | Rataiczak | ............... 134/111 X |
| 4,080,975 A | * 3/1978 | Williams | ............. 134/102.2 X |
| 4,086,929 A | * 5/1978 | Focht | ...................... 134/143 X |
| 5,464,033 A | * 11/1995 | Hartnell | .................. 134/111 X |
| 5,649,556 A | * 7/1997 | Braun | ........................ 134/92 |
| 5,711,328 A | * 1/1998 | Braun | ....................... 134/111 |
| 6,263,890 B1 | * 7/2001 | Hoser | ......................... 134/111 |
| 6,305,391 B1 | * 10/2001 | Hoser | ......................... 134/111 |

* cited by examiner

Primary Examiner—Randy Gulakowski
Assistant Examiner—Joseph Perrin
(74) Attorney, Agent, or Firm—Jackson Walker L.L.P.

(57) ABSTRACT

A cleaning apparatus for electric shaver components has a removable basket that fits inside a compartment. Cleaning is carried out by pumping cleaning fluid and air into a bottom of the compartment via a sieve plate. Debris removed from the components is collected in one compartment of a reservoir. The level of the water in the reservoir is maintained and controlled by the provision of an overflow pipe.

5 Claims, 1 Drawing Sheet

ELECTRIC SHAVER CLEANING APPARATUS

BACKGROUND OF THE INVENTION

1. Field of the Invention

The invention relates to apparatus for cleaning electric shavers.

2. Description of Prior Art

Electric shavers are widely used by men and women and usually, but not necessarily, powered by batteries. Most razors are not normally totally waterproof and anyway cannot be conveniently cleaned by being submerging in water. Even where the razors are waterproof, they cannot be comprehensively cleaned without disassembling the razor to some extent. At present, the cutting assemblies and hair grills require manual brushing and washing. Even where all the surfaces to be cleaned can be reached by brushing, the parts are often intricate and mechanically relatively delicate and so easily bent or otherwise damaged. Apart from this, cleaning is tedious and time consuming.

SUMMARY OF THE INVENTION

It is an object of the invention to overcome or at least reduce this problem.

According to the invention there is provided a cleaning apparatus for electric shaver components comprising an open topped cleaning compartment, a removable basket that fits inside the container for supporting the components, a pump that pumps cleaning liquid from a reservoir into the compartment, a liquid return flow path connecting the compartment to the reservoir and a debris collector to remove debris carried in the liquid returning to the reservoir.

Preferably, a liquid agitator is mounted in the cleaning compartment below the basket.

The agitator may be an air bubble generator.

The bubble generator may comprise a sieve plate.

The sieve plate may be in the form of a cone having a central region that allows air to enter the cleaning compartment.

The sieve plate may have a peripheral region through which cleaning liquid from the pump can pass into the cleaning compartment.

The liquid return flow path may have an upward facing valve outlet in the compartment, and the apparatus include a valve closure stopper loosely mechanically coupled to a compartment lid that fits down upon and closes off the valve outlet when the lid is closed over the top of the compartment.

The reservoir may have two chambers formed with a dividing wall comprising a filter that is positioned between a liquid inlet port and a liquid outlet port of the reservoir.

BRIEF DESCRIPTION OF THE DRAWINGS

A cleaning apparatus for cleaning components of electric shavers will now be described by way of example with reference to the accompanying drawing in which elevation of the apparatus.

DESCRIPTION OF THE PREFERRED EMBODIMENTS

Figure 1:
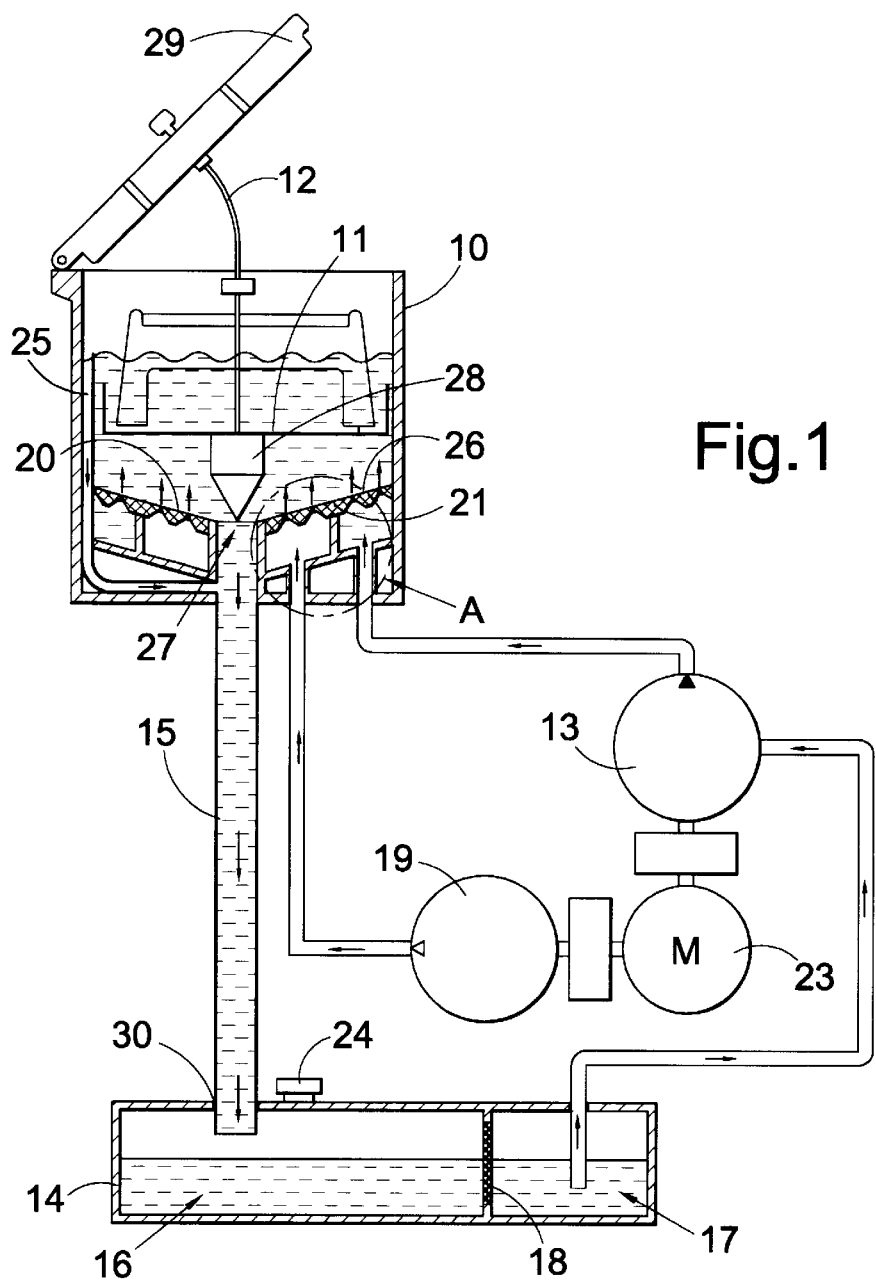
FIG. 1 is a sectional schematic view of the apparatus.

Referring to the drawings, in FIG. 1 an open topped compartment 10 is provided with a removable basket 11. The basket has a horizontal base and is supported by a cable 12, as explained below, inside the compartment. A liquid pump 13 pumps liquid from a reservoir 14 into a bottom of the compartment 10. A central return flow pipe 15 is provided to allow water to flow from the compartment back into the reservoir 14. The reservoir has two chambers 16 and 17 separated by a dividing wall 18 in the form of a filter.

In use, debris removed from shaver components placed in the basket 11 passes down the pipe 15 and is collected in the chamber 16.

Figure 2:
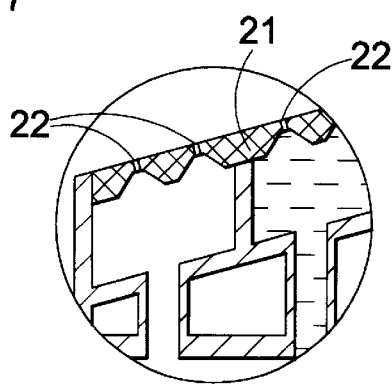
FIG. 2 is an enlarged part A of FIG. 1.

An air pump 19 supplies air into the bottom of the chamber 10 via a central region 20 of a sieve plate 21 to form small bubbles that rise up through and agitate liquid in the chamber 10 and in the basket 11. The sieve plate 21 is formed with apertures 22 (better seen in FIG. 2) that are shaped to have larger areas at a lower surface of the plate than at an upper surface. This aids formation of the small bubbles to improve the cleaning action. A single electric motor 23 is used to drive the pumps 13 and 19.

The reservoir 14 has filler cap 24 and the return flow pipe 15 is connected to an overflow drain pipe 25 that serves to maintain liquid in the reservoir 10 at a desired maximum level.

The apertures 22 in a peripheral region 26 of the sieve plate 21 control and allow cleaning liquid to pass upwards from the pump 13 into the cleaning compartment 10. A central aperture 27 of the sieve plate 20 forms an upward facing valve outlet. A closure stopper 28, mounted to a base of the basket 11, fits down upon and closes off the valve outlet 27 when a hinged lid 29 is closed over the top of the compartment 10; the closure stopper 28 being in effect loosely mechanically coupled to the lid by the cable 12.

In use, components of an electric shaver are placed in the basket for cleaning. Liquid, such as soapy sterilizing water, is placed in the reservoir and the motor 23 turned on. Water is pumped into the component 10 and returns via the overflow pipe 25 into the reservoir 14. Air bubbling through the liquid in the compartment cleans the shaver components and debris removed from the compartments is collected in the chamber 16 because the presence of the filter 18, which separates an inlet port 30 from an outlet port 31 of the reservoir. The reservoir can be removed and flushed out from time to time, usually after several cleaning operations, or as required.

It will be appreciated that the non-uniform apertures 21 compress the air to some extent as it passes through the sieve plate 20. As a result, small air bubbles that are created expand as they rise through the basket to increase the agitation they cause and to improve the cleaning effect.

The described apparatus serves to automatically and thoroughly clean the shaver components, even where the components have intricate shapes and crevices. Cleaning is carried out without placing any significant mechanical stresses on the components which may otherwise be strained or damaged.

A waterproof razor may be cleaned by placing a head of the razor in the basket without removing the shaving operative parts from the head. In such a case, if the lid 27 cannot be closed, the cable 12 must be disconnected.

I claim:

1. A cleaning apparatus for electric shaver components comprising an open topped cleaning compartment, a removable basket that fits inside the container for supporting the components, a pump that pumps cleaning liquid from a reservoir into the compartment, a liquid return flow path connecting the compartment to the reservoir and a debris collector to remove debris carried in the liquid returning to the reservoir; a liquid agitator mounted in the cleaning compartment below the basket, the agitator being an air bubble generator, the bubble generator having a sieve plate, the sieve plate is in the form of a cone having a central region that allows air to enter the cleaning compartment.

2. A cleaning apparatus according to claim 1, in which the sieve plate has a peripheral region through which cleaning liquid from the pump can pass into the cleaning compartment.

3. A cleaning apparatus for electric shaver components comprising:

a reservoir for a quantity of cleaning liquid, an open topped cleaning compartment, a removable basket that fits inside the compartment for supporting the components, a pump for pumping cleaning liquid from the reservoir into the compartment, a liquid return flow path connecting the compartment to the reservoir, a debris collector for removing debris carried in the liquid returning to the reservoir, and an agitator comprising a cone having a central region that allows air to enter the cleaning compartment.

4. A cleaning apparatus according to claim 3, in which the liquid return flow path has an upward facing valve outlet in the compartment, and including a valve closure stopper, loosely mechanically coupled to a compartment lid, that fits down upon and closes off the valve outlet when the lid is closed over the top of the compartment.

5. A cleaning apparatus according to claim 3, in which the reservoir has two chambers formed with a dividing wall comprising a filter that is positioned between a liquid inlet port and a liquid outlet port of the reservoir.

* * * * *